United States Patent [19]
Geisinger et al.

[11] Patent Number: 5,457,054
[45] Date of Patent: Oct. 10, 1995

[54] UNIT TEST KIT AND METHOD FOR QUALITATIVE IDENTIFICATION OF AN ILLICIT DRUG

[76] Inventors: George H. Geisinger, 358 Summit Rd., Mountainside, N.J. 07092; Kenneth R. Fitzpatrick, 56 Pine Hill Dr., Upper Saddle River, N.J. 07458; L. J. Scott, 133 Red Oak Dr., Flower Mound, Tex. 75028

[21] Appl. No.: 342,403

[22] Filed: Nov. 18, 1994

Related U.S. Application Data

[63] Continuation of Ser. No. 25,141, Mar. 2, 1993, abandoned.

[51] Int. Cl.$^6$ .......................... G01N 33/94; G01N 33/48
[52] U.S. Cl. .......................... 436/92; 436/808; 436/901; 422/61; 422/56; 422/58
[58] Field of Search ................... 422/56–58, 61; 436/808, 901, 166, 164

[56] References Cited

U.S. PATENT DOCUMENTS

| | | | |
|---|---|---|---|
| 3,955,926 | 5/1976 | Fischer | 422/61 |
| 4,132,527 | 1/1979 | Maekawa et al. | 422/56 |
| 4,196,167 | 4/1980 | Olsen | 422/61 |
| 4,752,448 | 7/1988 | Wells et al. | 436/901 |
| 4,806,487 | 2/1989 | Akers et al. | 436/901 |

Primary Examiner—Lyle A. Alexander

[57] ABSTRACT

A self-contained unit test for qualitative identification of suspect substances including cocaine, heroin and cannabis, includes a visualization reagent having a compound which undergoes a visible color change when contacted by a suspect substance. The unit test further includes a pad formed from a bibulous material impregnated with the reagent and a unit package for containing the pad and maintaining the reagent in an as-filled, ready-to-use state during storage. A method for visualization of a suspect substance with a unit test of the present invention includes providing a unit test for a suspect substance which includes a visualization reagent for qualitative identification of a suspect substance impregnated on a pad formed from a bibulous material, and sealed in a unit package. The method further includes opening the package, and wiping the pad on as sample containing the suspect substance. The pad surface is then observed for any color changes, the color change being indicative of contact with the suspect substance. A kit for qualitative identification of a suspect substance includes one or more of one or all of the self contained unit tests for the visualization of suspect substances, instructions for use and an over package. The kit may further include non-destructive sample collection pads, disposable gloves, sealable inert evidence collection bags and labels.

7 Claims, 2 Drawing Sheets

5,457,054

UNIT TEST KIT AND METHOD FOR QUALITATIVE IDENTIFICATION OF AN ILLICIT DRUG

This application is a continuation of application Ser. No. 08/025,141, filed Mar. 2, 1993, now abandoned.

FIELD OF THE INVENTION

The present invention relates to qualitative identification of a suspect substance and more particularly to a kit with self-contained unit-tests for visualization of the presence of controlled substances such as cocaine, heroin, and tetrahydrocannabinol (cannabis).

DESCRIPTION OF RELATED INFORMATION

Generally speaking, tests for qualitative identification of a suspect substance consist of a reagent or reagents, a sampling apparatus and a vessel for mixing the reagent with the sample and observing the result. There have been efforts to make the tests easier to use by packaging the reagents in unit dose ampules, self measuring sampling devices and combinations of sampling devices and test vessels. The use of ampules for reagents improved the ease and safety of handling the identification reagent, some of which are toxic and corrosive. These sampler, reagent, vessel devices are satisfactory for identifications of suspect substances, but have proved to be time consuming, are often difficult to use in the field and are not practical for broad or covert screening of luggage pieces, clothing and the like for trace amounts of suspect substances such as heroin, cocaine and cannabis derivatives.

Currently, in such screening situations, investigators use dogs which have been trained to react to the odor of the suspect substances. Additionally, there are sprays available which induce a color development when sprayed on a specific substance. The use of spray reagents which leave a residue is generally precluded in screening situations by liability considerations. Further, compounds present in some qualitative identification reagents are toxic and corrosive, obviously limiting the ability of investigators to use them in screening situations.

The task of investigators screening for suspect substances would be made easier if a self contained unit test was available which could be easily and rapidly used, which did not leave residue behind. Additionally, if such tests were provided in a kit which included one or more qualitative identification unit tests for several substance as well as a recovery system for acquisition of evidentiary samples, the task of investigators would be further facilitated. Such unit tests and kits, as well as methods for their use, are described herein below.

SUMMARY OF THE INVENTION

A self-contained unit test of the present invention for qualitative identification of a suspect substance includes a visualization reagent solution having a compound which undergoes a visible color change when contacted by a suspect substance. The unit test further includes a pad formed from a bibulous material impregnated with the reagent solution and a unit package for containing the pad and maintaining the reagent solution in an as-filled, ready-to-use state during storage.

A self-contained unit test of the present invention for qualitative identification of cocaine includes a visualization reagent prepared as an aqueous solution of cobaltous thiocyanate, glycerin, tartaric acid and boric acid, and a bibulous pad impregnated with the reagent solution. The pad containing the solution is sealed in a unit package to maintain the reagent on the pad in an as-filled, ready-to-use state during storage.

A self-contained unit test of the present invention for qualitative identification of heroin includes a visualization reagent prepared as a methanolic solution of cobaltous thiocyanate, ammonium metavanidate and yellow dye, and a bibulous pad impregnated with the reagent solution. The pad containing the solution is sealed in a unit package to maintain the reagent on the pad in an as-filled, ready-to-use state during storage.

A self-contained unit test of the present invention for qualitative identification of tetrahydrocannabinol (THC) includes a visualization reagent prepared as an aqueous ethanolic solution of ortho-dianisidine, and a bibulous pad impregnated with the reagent solution. The pad containing the solution is sealed in a unit package to maintain the reagent on the pad in an as-filled, ready-to-use state during storage.

A kit for the qualitative idemification of suspect substances of the present invention includes at least one self-contained unit test for qualitative identification of a suspect substance comprising a visualization reagent including a solution which undergoes a visible color change when contacted with a suspect substance, a bibulous pad impregnated with the visualization reagent, and a unit package for containing the pad. The package serves to maintain the reagent on the pad in an as-filled, ready-to-use state during storage. The kit further includes instructions for using the unit test and an over package for containing the unit test or tests and the instructions.

A method for visualization of a suspect substance on a surface of a sample includes providing a unit test including a visualization reagent for the suspect substance, a pad formed from a bibulous material having a surface and impregnated with the visualization reagent. The pad is additionally sealed in a unit package for maintaining the reagent in an as-filled, ready-to-use condition. The pad is removed from the package and wiped on the surface of the sample having the suspect substance. The pad surface is then observed for any color change, the color change being indicative of contact with the suspect substance.

DETAILED DESCRIPTION OF THE PREFERRED EMBODIMENTS

Figure 1:
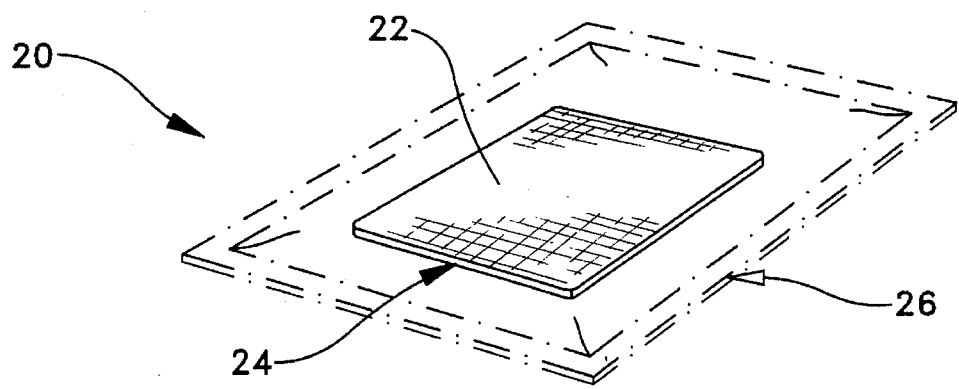
FIG. 1 is a perspective view of a pad of the present invention showing the unit package in phantom.

While this invention is satisfied by embodiments in many different forms, there is shown in the drawings and will herein be described in detail, preferred embodiments of the invention with the understanding that the present disclosure is to be considered exemplary of the invention and is not intended to limit the invention to the embodiments illustrated. The scope of the invention will be measured by the appended claims and their equivalents.

A self contained unit test of the present invention for qualitative identification of a suspect substance is illustrated in FIGS. 1–4 and is generally designated as 20. Referring to FIG. 1, the unit test 20 includes a visualization reagent 22 which undergoes a visible color change when contacted by a suspect substance. The visualization reagent 22 is impregnated onto a pad 24 formed from a bibulous material which serves to hold reagent 22 and deliver it for contacting a suspect substance.

Pad 24 impregnated with reagent 22 is contained in a unit package 26 which serves to maintain reagent 22 in an as-filled, ready-to-use state during storage.

A first preferred embodiment of unit test 20 is as a qualitative identification test for cocaine, here considered either as the free base, $C_{17}H_{21}NO_4$, as a salt of the base, or when mixed with common diluents.

The visualization reagent for cocaine includes preferably about 0.1 to about 10 percent, most preferably about 0.86 percent cobaltous thiocyanate; preferably about 0.1 to about 10 percent, most preferably about 0.86 percent, tartaric acid; preferably about 0.1 to about 10 percent, most preferably about 0.86 percent boric acid; preferably about 30 to about 65 percent, most preferably about 54.3 percent glycerin; and water, preferably in a quantity sufficient to make 100 percent, most preferably 43.1 percent. The ingredients are placed in a clean vessel at ambient temperature and stirred until solid components are substantially dissolved.

Pad 24 is formed from a bibulous material which preferably is a fibrous nonwoven, such as cotton, rayon, polyester, blends of cotton, rayon, polyester, and most preferably is formed from nonwoven rayon with a basis weight of 160 grams.

Preferably about 0.5 to 1.5 ml, and most preferably about 0.8 ml of the cocaine visualization reagent is applied to pad 24 which preferably is sized to fit in the hand of the user, most preferably about 2.5×3.4 cm. Pad 24 impregnated with the preferred cocaine visualization reagent is preferably sealed in an appropriately labeled unit package which is formed from materials which serve to maintain reagent 22 in an as-filled, ready-to-use state during storage. An example of the first preferred visualization reagent 22, when the suspect substance is cocaine, is given as Example 1.

EXAMPLE 1

Preparation of a unit-test for qualitative identification of cocaine.

I. Cocaine Visualization Reagent

In a clean, well-stirred mixing vessel place the following components (all values in parts per hundred; w./wt.):

1. 43.11-water (meeting USP criteria for purified water);
2. 0.86-cobaltous thiocyanate (Sigma C-5637 or eq.);
   stir for about 1 hour at ambient temperature to effect dissolution, then add;
3. 54.3 1-glycerin (USP grade);
4. 0.86-tartaric acid (USP grade);
5. 0.86-boric acid (USP grade); and
   continue stirring at ambient temperature to a substantially uniform solution.

II. Pad Preparation

To a nonwoven rayon pad (e.g. Champion Edison 160 gram nonwoven rayon, M.P.D. 24-001) 2.54cm×3.4 cm, add 0.8 ml of the above cocaine visualization reagent.

III. Package Preparation

Each individual pad impregnated with 0.8 ml of the above cocaine visualization reagent is sealed in a package formed from an upper web and a lower web both composed of ethylene-acrylic acid copolymer/aluminum foil/polyethylene/paper to form a package resistant to moisture and air permeation which is capable of maintaining the unit-test in an as-filled, ready-to-use state during storage.

IV. Function

An unused pad impregnated with the above cocaine visualization reagent has a light pink color. When the surface of the pad contacts cocaine, the area of contact develops a blue color, similar to Pantone Process Blue, indicating the presence of cocaine.

A second preferred embodiment of unit test 20 is as a qualitative identification test for heroin, here considered either as the free base $C_{21}H_{23}NO_5$ as a salt of the base or when mixed with common diluents.

The visualization reagent for heroin includes preferably a methanolic solution about 0.1 to about 10 percent, most preferably about 1.25 percent of cobaltous thiocyanate; preferably about 0.05 to about 5.0 percent, most preferably about 0.28 percent, metavanidate; about 0.01 to about 1 percent, most preferably about 0.63 percent, aqueous yellow dye and methyl alcohol, preferably in a quantity sufficient to make 100 percent, most preferably 97.86 percent. The cobaltous thiocyanate and the ammonium metavanidate are both prepared as stock solutions, then filtered, with the filtrates being mixed with the yellow dye to complete the preparation of the heroin visualization reagent.

Preferably about 0.1 to about 1.5 ml, and most preferably about 0.8 ml, of the heroin visualization reagent is applied to pad 24 which is sized to fit in the hand of the user, most preferably about 2.5 by 3.4 cm. Pad 24 impregnated with the preferred heroin visualization reagent is preferably sealed in an appropriately labeled unit package which is formed from materials which serve to maintain reagent 22 in an as filled ready-to-use state during storage. An example of the second preferred visualization reagent 22, when the suspect substance is heroin is given as Example 2.

EXAMPLE 2

Preparation of a unit test for qualitative identification of heroin.

I. Heroin Visualization Reagent

Prepare the following stock solutions:

A.) Stir 2.0 gm cobaltous thiocyanate (Sigma C-5637 or eq.) into 48 gm methanol (Reagent Grade) for 5 min. at ambient temperature; filter (Whatman #1 or eq.); filtrate is solution A;

B.) Stir 0.5 gm ammonium metavanidate (Aldrich 20,555-9 or eq.) into 160 gm methanol (Reagent Grade), filter (Whatman # 1 or eq.); filtrate is solution B; and C.) Solution C is aqueous yellow dye (McCormick UPC#07092 or eq.).

In a clean well stirred vessel, mix at ambient temperature, 24 gm of solution A with 56 gm of solution B and 1 gm of solution C; stir to a substantially uniform solution to form the heroin visualization reagent.

II. Pad preparation

To a nonwoven rayon pad (e.g. Champion Edison 160 gm nonwoven rayon, M.P.D. 24-001) 2.5 by 3.4 cm add 0.8 ml of the above heroin visualization reagent.

III. Package Preparation

Each individual pad impregnated with 0.8 ml of the above heroin visualization is sealed in a package formed from an upper web and a lower web both composed of ethylene-acrylic acid copolymer/aluminum foil/ polyethylene/paper. This forms a package, resistant to moisture and air permeation, which is capable of maintaining the unit test in an as-filled, ready-to-use state during storage.

IV. Function

An unused pad impregnated with the above heroin visualization reagent has a pale yellow color. When the surface of the pad contacts heroin, the area of contact develops a light green color, similar to Pantone 340C, indicating the presence of heroin.

A third preferred embodiment of unit test 20 is as a qualitative identification test for delta 9-tetrahydrocannabinol, $C_{21}H_{30}O_2$, including but not limited to marijuana, hashish and hash oil. For the purposes of this document, all tetrahydrocannabinol containing substances will hereinafter be referred to as "THC".

The visualization reagent for THC includes preferably about 0.09 to about 10 percent, most preferably about 0.35 percent ortho-dianisidine; and preferably sufficient aqueous 60 percent ethyl alcohol to make 100 percent, most preferably 99.65 percent. The ortho-dianisidine preferably is well mixed with the aqueous ethanol, then filtered, the filtrate being the reagent.

Preferably about 0.5 to 1.5, ml and most preferably about 0.8 ml, of the heroin visualization reagent is applied to pad 24 which is sized to fit in the hand of the user, most preferably about 2.5 by 3.4 cm. Pad 24 impregnated with the preferred THC visualization reagent is preferably sealed in an appropriately labeled unit package which is formed from materials which serve to maintain reagent 22 in an as-filled ready-to-use state during storage. An example of the third preferred visualization reagent 22 when the suspect substance is THC is given as Example 3.

EXAMPLE 3

Preparation of a unit test for qualitative identification of tetrahydrocannabinol (THC).

I. THC visualization reagent

Stir 0.3 gm of ortho-dianisidine (Sigma D-3502 or eq.) into 85 gm of 60 percent aqueous ethanol (45 gm Baker 5-9401 or eq. and 40 gm Water [meeting USP criteria for purified water] at ambient conditions; filter (Whatman #1 or eq.); filtrate is the THC reagent.

II. Pad preparation

To a nonwoven rayon pad (e.g. Champion Edison 160 gm nonwoven rayon, M.P.D. 24-001) 2.5 by 3.4 cm add 0.8 ml of the above THC visualization reagent.

III. Package Preparation

Each individual pad impregnated with 0.8 ml of the above THC visualization reagent is sealed in a package formed from an upper web and a lower web both composed of ethylene-acrylic acid copolymer/aluminum foil/polyethylene/paper. This forms a package, resistant to moisture and air permeation, which is capable of maintaining the unit test in an as-filled, ready-to-use state during storage.

IV. Function

An unused pad impregnated with the above THC visualization reagent has an off-white color. When the surface of the pad contacts a material containing THC, the area of contact develops a red-brown color, similar to Pantone 201 C, in one to two minutes at ambient temperature indicating the presence of THC. Color development and identification maybe facilitated by folding the contact surface back onto itself, thereby assuring that both sides of any suspect particulate comes in contact with the reagent.

Figure 2:
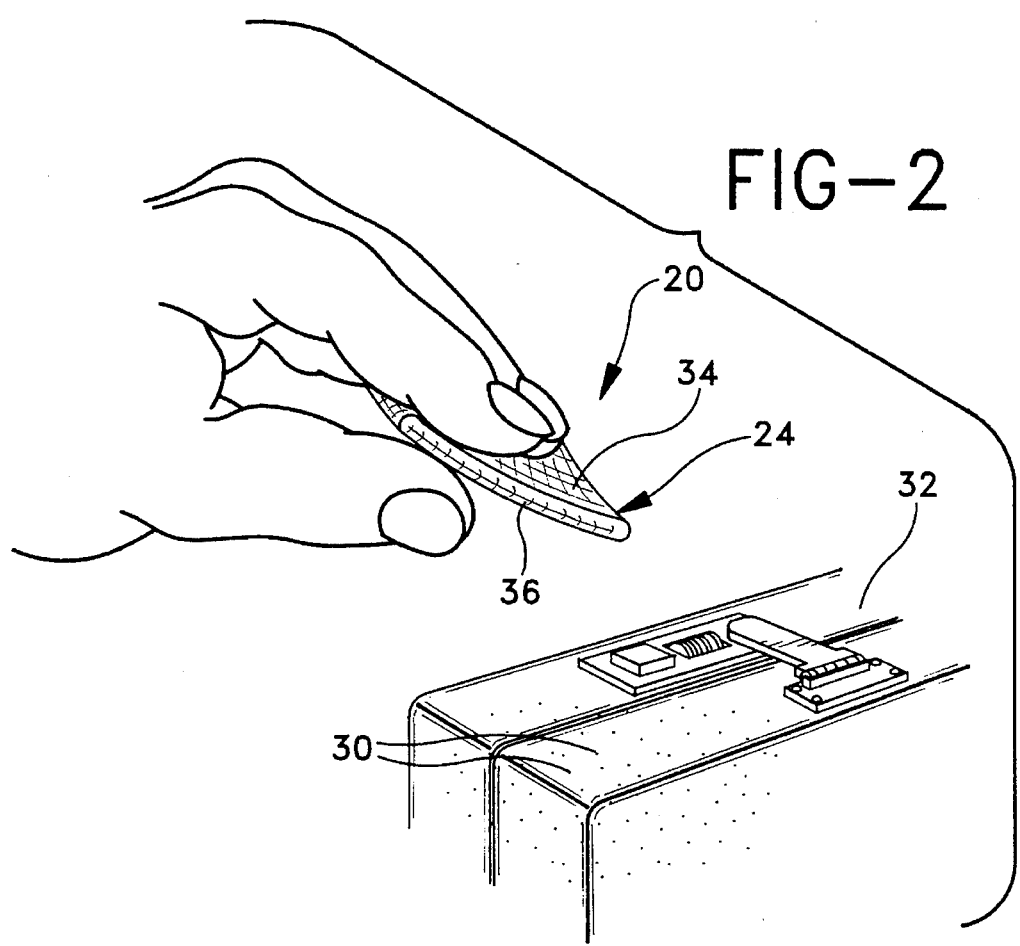
FIG. 2 is a sketch showing the usage of the pad of the present invention to identify a suspect substance on a surface.

In cases where a positive identification for a suspect substance is made using one of the preferred self contained unit tests described herein above, rules of evidence require that additional samples be acquired in an unaltered state for confirmatory assay by alternate analytical methods using reference standard compounds. To assist investigators in acquiring these evidentiary samples, a kit may include instructions, one or more of one or all of the self contained unit tests for visualization of suspect substances. The kit may also include a pad, as shown in FIGS. 1 and 2 as pad 24, impregnated with 70 percent aqueous isopropyl alcohol. This pad may be used for wiping a surface or an article which qualitatively test positively for a suspect substance to pick up the substance from the surface without changing it. The pad with the unchanged suspect substance may then be placed in a clean inert plastic bag and sealed. The kit may include such bags for containing and protecting the pad with the sample, as well as appropriate labels. Preparation of a sample collection pad is described as Example 4.

EXAMPLE 4

Non-Destructive Sample Collection Pad

I. Collection Reagent 70 percent isopropyl alcohol (USP or eq.)

II. Pad preparation

To a nonwoven rayon pad (e.g. Champion Edison 160 gm nonwoven rayon, M.P.D. 24-001) 2.5 by 3.4 cm, add 0.8 ml of the above collection reagent.

III. Package Preparation

Each individual pad impregnated with 0.8 ml of the above collection reagent is sealed in a package formed from an upper web and a lower web both composed of ethylene-acrylic acid copolymer/aluminum foil/ polyethylene/paper. This forms a package, resistant to moisture and air permeation, which is capable of maintaining the collection reagent pad in an as-filled, ready-to-use state during storage.

IV. Function

An unused pad impregnated with collection reagent is used to wipe a surface containing substances for confirmatory analysis. The pad containing the substances is then placed in an inert evidence collection bag, sealed, and labeled.

A method for using unit test 20 for visualizing a suspect substance is shown in FIG. 2. Unit test 20 is provided, then pad 24 containing reagent 22 is removed from unit package 26. The to be tested sample 28 contains a suspect material 30 on its surface 32. Pad 24 has an upper surface 34 and a lower surface 36. For the purposes of conducting the test, either surface is identical. The operator wipes surface 32, containing suspect substance 30 thereon, with surface 36 of pad 24. Both pad 24 and surface 32 may be at ambient temperatures. On pad surface 36 which contacts sample surface 32, a color change 38 will occur in any area which contacted suspect substance 30.

In the first preferred embodiment, where visualization reagent 22 is a qualitative identification for cocaine, unused pad surface 36 has a light pink color. Color change 38 would develop as a blue color in the case where suspect substance 30 was cocaine.

In the second preferred embodiment, where visualization reagent 22 is a qualitative identification for heroin, unused pad surface 36 has a pale yellow color. Color change 38 would develop as a light green color in the case where the suspect substance was heroin.

In the third preferred embodiment, where visualization reagent 22 is a qualitative identification for THC, unused pad surface 36 has an off-white color. Color change 38 would develop after one to two minutes as a red-brown color where the suspect substance is THC.

Figure 3:
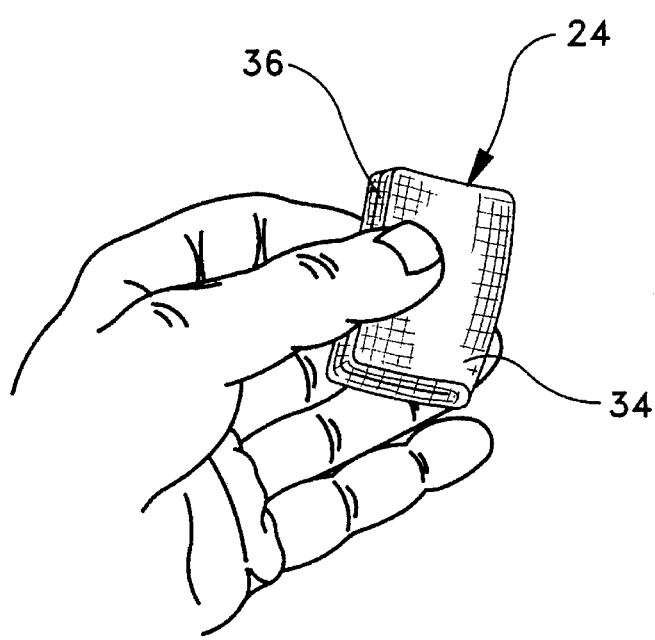
FIG. 3 is a sketch showing the surface of the pad of the present invention folded upon itself after contacting surface which may have thereon particles of a suspect substance.
Figure 4:
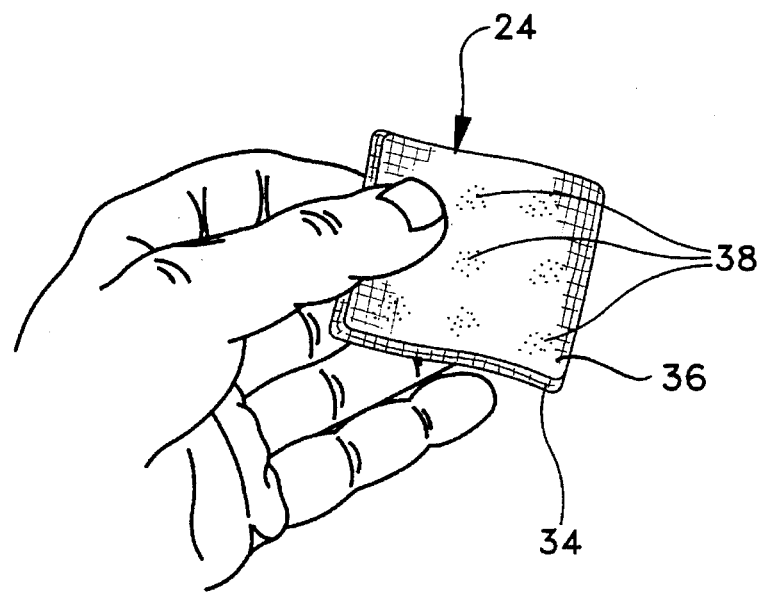
FIG. 4 is a sketch showing the surface of the pad of the present invention after contacting a surface having thereon particles of a suspect substance.

In all cases, but particularly for the THC reagent, the development of the color may be facilitated by folding the wiping surface over on itself, as shown in FIG. 3. This folding enhances contact of the visualization reagent with both sides of any particles picked up during wiping, thereby enhancing the sensitivity of the test to the presence of any suspect substance.

One skilled in the art of qualitative identification of suspect substances will recognize that the size and composition of the pad, the amount of the visualization reagent and the composition of the visualization reagent itself may be varied to accommodate particular applications and particular suspect substances. Kits may be prepared with multiple tests for multiple substances in a pack including instructions for use, color comparison charts, non-destructive evidence collection pads, inert sealable evidence collection bags, labels and the like as well as disposable gloves. The use of disposable gloves would help to ensure that any positive test result obtained was due only to materials present on the surface of the article being tested and further, that any sample collected using the sample collection pad was uncontaminated.

Thus, it can be seen that the present invention provides the art and practitioners of qualitative identification of suspect substances with a simple, easily used unit test, kit and method suitable for screening, qualitative identification and evidence collection.

We claim:

1. A method for visualizing an illicit drug on a surface of a sample comprising:

providing a unit-test comprising a liquid visualization reagent solution for an illicit drug, a pad having a surface, said pad formed from a bibulous material impregnated with said visualization reagent, and a unit package for containing said pad with said reagent for maintaining said reagent in a ready-to-use state during storage, wherein said visualization reagent solution includes a visualization reagent for qualitative identification of THC comprising (wt./wt.):

about 0.05 to 10 percent ortho-dianisidine and sufficient aqueous 60 percent ethyl alcohol to make 100 percent;

opening said package;

removing said pad;

wiping the surface of the sample with said surface of said pad; and observing said surface of said pad for a color change from an off-white to a red-brown color in any area where said surface of said pad containing said visualization reagent is contacted with THC.

2. A self contained unit test for qualitative identification of THC comprising:

a liquid visualization reagent comprising an aqueous ethanol solution of ortho-dianisidine, said visualization reagent undergoing a color change from an off-white to a red-brown upon contacting THC;

a bibulous pad impregnated with said reagent; and a unit package for containing said pad, said package maintaining said reagent on said pad in a ready-to-use state during storage.

3. The self contained unit test of claim 2 wherein said pad is formed from a material selected from the group consisting of cotton, rayon, polyester and blends thereof.

4. The self contained unit test of claim 2 wherein said pad is formed from a nonwoven rayon having from about 0.5 to 1.5 grams of said aqueous visualization reagent applied thereto.

5. The self contained test unit of claim 2 wherein said unit package is formed by sealing an upper web and a lower web, said webs being formed from a composite selected from the group consisting of paper, aluminum foil, polyethylene and ethylene-acrylic acid copolymer and combinations thereof.

6. The self contained unit test of claim 2 wherein said reagent comprises (wt./wt.) about 0.05 to about 10 percent ortho-dianisidine and sufficient 60 percent aqueous ethanol to make 100 percent.

7. The self contained unit test of claim 2 further comprising:

said reagent comprising (wt./wt.; pans/hundred) 0.35 ortho-dianisidine and 99.65 aqueous 60 percent ethanol; and said reagent stirred to a substantially uniform content with about 0.8 ml of said reagent applied to said pad, said pad being 160 gm basis weight nonwoven rayon about 2.5 by 3.4 cm.

* * * * *